United States Patent
Mihajlovic et al.

(10) Patent No.: US 9,036,140 B2
(45) Date of Patent: May 19, 2015

(54) OPTICAL PROBE SYSTEM WITH INCREASED SCANNING SPEED

(75) Inventors: Nenad Mihajlovic, Eindhoven (NL); Jeroen Jan Lambertus Horikx, Eindhoven (NL); Waltherus Cornelis Jozef Bierhoff, Eindhoven (NL); Cornelius Antonius Hezemans, Nuenen (NL); Bernardus Hendrikus Wilhelmus Hendriks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 353 days.

(21) Appl. No.: 13/496,213

(22) PCT Filed: Sep. 10, 2010

(86) PCT No.: PCT/IB2010/054095
§ 371 (c)(1),
(2), (4) Date: Mar. 15, 2012

(87) PCT Pub. No.: WO2011/036598
PCT Pub. Date: Mar. 31, 2011

(65) Prior Publication Data
US 2012/0170030 A1 Jul. 5, 2012

(30) Foreign Application Priority Data
Sep. 24, 2009 (EP) .................... 09171165

(51) Int. Cl.
*G01J 1/00* (2006.01)
*A61B 5/00* (2006.01)
*G02B 26/10* (2006.01)

(52) U.S. Cl.
CPC .............. *A61B 5/0062* (2013.01); *A61B 5/0084* (2013.01); *G02B 26/103* (2013.01)

(58) Field of Classification Search
CPC ...... A61B 1/07; A61B 5/0066; A61B 5/0062; A61B 5/0084; G01B 2290/65; G01B 9/0205; G01B 9/02091; G02B 26/103
USPC .......... 356/213, 479, 497, 609; 600/160, 368, 600/425, 476
See application file for complete search history.

(56) References Cited

U.S. PATENT DOCUMENTS 5,659,392 A * 8/1997 Marcus et al. ................ 356/497
6,485,413 B1 * 11/2002 Boppart et al. ............... 600/160
(Continued)

FOREIGN PATENT DOCUMENTS

| | | |
|---|---|---|
| JP | 2001174744 | 6/2001 |
| JP | 2003535659 | 12/2003 |

(Continued)

*Primary Examiner* — Baisakhi Roy

(57) ABSTRACT

An optical probe system having a probe with an optical guide (G) having a distal end. The optical guide (G) is mounted inside a housing (H) so that the distal end is displaceable with respect to the housing (H). A set of actuators (A), e.g. electromagnetic drive coils, can displace the distal end by application of a drive signal ($V_x$, $V_y$). A control unit (CU) generates the drive signal ($V_x$, $V_y$) so as to provide a scanning frequency which varies according to an amplitude of the drive signal ($V_x$, $V_y$). With such probe system it is possible to scan a field of view with a scanning frequency that varies with the scanning radius. Taking into account the maximum allowable drive current, it is possible to increase scanning speed compared to scanning at the mechanical resonance frequency of the optical system, since small radii can be scanned at a high scanning frequency.

15 Claims, 3 Drawing Sheets

(56) References Cited

U.S. PATENT DOCUMENTS

| | | |
|---|---|---|
| 7,129,472 B1 | 10/2006 | Okawa et al. |
| 8,466,956 B2 | 6/2013 | Sugimoto et al. |
| 2002/0064341 A1 | 5/2002 | Fauver et al. |
| 2002/0161282 A1* | 10/2002 | Fulghum .................. 600/160 |
| 2003/0004412 A1* | 1/2003 | Izatt et al. ................ 600/425 |
| 2006/0170930 A1* | 8/2006 | Li ............................. 356/479 |
| 2008/0058629 A1* | 3/2008 | Seibel et al. .............. 600/368 |
| 2008/0130014 A1* | 6/2008 | Rush ......................... 356/609 |
| 2008/0218824 A1 | 9/2008 | Johnston et al. |
| 2008/0265178 A1 | 10/2008 | Johnston |

FOREIGN PATENT DOCUMENTS

| | | |
|---|---|---|
| JP | 2007272011 | 10/2007 |
| JP | 2010142482 | 1/2010 |
| WO | WO0197902 | 12/2001 |
| WO | WO2006041459 | 4/2006 |
| WO | WO2008133636 | 11/2008 |

* cited by examiner

OPTICAL PROBE SYSTEM WITH INCREASED SCANNING SPEED

FIELD OF THE INVENTION

The present invention relates to an optical probe suitable for miniature applications.

BACKGROUND OF THE INVENTION

In connection with diagnosis of various diseases, such as various cancer diseases, biopsies are taken. When taking a biopsy and no malignant cells are detected, it is important that it can be ruled out that this is not simply due to that the biopsy was sampled from the wrong site. To increase the certainty of the biopsy sampling, guided biopsy may be used. Such guided biopsy sampling can be based on a number of image modalities, examples include X-ray, CT, MRI, ultrasound and optics.

For many purposes optical imaging by use of a miniaturized needle microscope is used. Imaging by use of needle microscopy has the advantage that it does not involve harmful X-rays or the expensive machinery of CT or MRI scanners. Moreover, it supports integration into the biopsy needle itself, thereby allowing direct visual inspection of the biopsy site prior to, during and after the biopsy.

In prior art, optical probe systems for medical applications scan over a field of view by means of an electromagnetically driven optical fibre system which is used to scan over a field of view. The whole field of view is scanned with a scanning frequency coinciding with a mechanical resonance frequency of the moving parts of the optical fibre system. Hereby it is possible to obtain an efficient scanning with the use of a limited drive current, thereby meaning that a reasonable scanning speed can be obtained with a limited heat dissipated by the miniature drive coils.

However, the inventor of the present invention has appreciated that in the mentioned prior art optical probe system, the scanning speed is limited by the limited scanning frequency, which again influences the time required for a sufficient scanning image—an important factor within medical applications.

SUMMARY OF THE INVENTION

It would be advantageous to achieve an optical probe system suited for use in a miniature medical device, capable of providing a high scanning speed, still without problems with heat produced by the drive elements. Especially, it would be desirable to obtain a scanning speed exceeding the speed that can be obtained by scanning the field of view at a scanning frequency equal to the mechanical resonance frequency of the moving parts. An increased scanning speed can be used to provide better patient comfort since the medical treatment, e.g. biopsy, can be executed faster. Alternatively, the increased speed can be used to increase image resolution in the captured images, and thus provide a better image quality at the same capturing time. In general, the invention preferably seeks to mitigate, alleviate or eliminate one or more of the above mentioned disadvantages singly or in any combination. In particular, it may be seen as an object of the present invention to provide a system and a method that solves the above mentioned problems, or other problems, of the prior art.

In a first aspect, the invention provides an optical probe system comprising
a probe comprising
an optical guide having a distal end,
a housing, the optical guide being mounted inside the housing so that the distal end is displaceable with respect to the housing, and
an actuation system, e.g. an electromagnetic actuation system, comprising a set of actuators capable of displacing the distal end by a displacement force induced by applying a drive signal to the set of actuators, and
a control unit operationally connected to the probe, the control unit being arranged to generate the drive signal to the set of actuators so as to displace the distal end according to a scanning form over a field of view, wherein the control unit generates the drive signal so as to provide a scanning frequency which varies according to an amplitude of the drive signal.

By providing an electric drive signal to the actuators such that the scanning frequency varies according to an amplitude of the drive signal, it is possible to obtain a variable scanning frequency over the field of view. Hereby, it is possible to obtain a scanning speed which exceeds the speed that can be obtained by providing a fixed scanning speed over the field of view, still without problems with too much heat from the drive elements, e.g. drive coils.

In prior art optical probe systems, in order to be able to work at frequencies close to the resonance frequency, the targeted area is scanned using spirals consisting of circular or elliptical lines. The maximum radius that can be scanned is limited by the maximum current that can be applied to the driving coils without overheating them, i.e. assuming there are no geometrical constraints on the maximum allowed radius. Higher drive currents cause higher heat dissipation from the actuators, e.g. coils. However, in case the system scans a circle with a radius that is smaller than the maximum radius, currents are used which are below the maximum allowed current. Consequently, it is possible in that case to scan the same line with a frequency higher than the resonance frequency, which will demand a higher current to reach the same radius, but still without exceeding the maximum allowed current. Thus, in preferred embodiments, the heat dissipation is monitored, and thus the scanning frequency can be chosen to be as high as possible but not so high as to overload the actuators. With such increased scanning speed at small radii, the total scanning speed can be increased compared to the constant scanning speed prior art systems.

In preferred embodiments, the control unit generates the drive signal such that the amplitude of the drive signal varies during scanning over the field of view. This may especially be obtained by applying drive signals to the set of actuators comprising a set of harmonic signals, such as a set of two harmonic signals being 90° out of phase, and wherein the set of actuators comprises two actuators are arranged in relation to each other 90° spaced apart.

The set of actuators may comprise one or several types of different actuator types, such as electromagnetic and/or piezoelectric types. Thus, the set of actuators may comprise at least one of: an electrically conductive coil, and a piezoelectric element.

The scanning over the field of view may be performed by applying drive signals to the set of actuators causing a scanning in a spiral form or scanning in Lissajous figures.

In a preferred embodiment, the drive signal is limited in accordance with a predefined maximum value determined by the set of actuators, such as the drive signal being limited according to a maximum defined drive current to provide a safe operation of the specific actuators used, e.g. determined by a maximum allowed drive current for electromagnetic drive coils.

The drive signal may be limited in accordance with a measure of temperature of the set of actuators, hereby it can be ensured that safe operation of the drive coils without too high temperatures. This is especially important within medical applications where high temperatures may cause harm to a patient, e.g. in case the optical probe is used as a biopsy needle arranged for insertion in the tissue a patient. In embodiments where the set of actuators are electrically conductive coils, the measure of temperature of the electrically conductive coils may be deducted by measurement of electrical resistance of at least one of the electrically conducive coils. This solution saves space for a dedicated temperature sensor.

The optical probe may comprise a measuring transducer arranged to measure a position of the optical fibre, e.g. in the form of a coil-based transducer. Hereby, it is possible to monitor the actual position of the optical fibre, and thus get a feedback of the actual scanning position. Especially, the control unit may comprise a position set-point generator and a position-control unit, wherein the position-control unit is operationally connected to the measuring transducer. Hereby, it is possible to precisely control the movement of the optical fibre and thereby the scanning pattern.

Especially, the optical guide is an optical fibre with a free distal end, and the free distal end preferably forms an optical lens. The optical fibre is preferably arranged to guide at least one of: visible light such as laser light, Light Emitting Diode light or other light sources. Especially, the optical probe may be arranged for confocal scanning.

The optical probe system is suited for medical applications, and thus in preferred embodiments, the optical probe forms part such as an endoscope, a catheter, a needle or a biopsy sample system. In the medical applications, the advantages of the probe system are increased patient comfort due to the increased scanning speed which can be used to reduce the time needed for the potentially uncomfortable medical examination, or alternatively increase the scanning precision to ensure that the relevant position in the human tissue is examined, e.g. a tumor, thus avoiding repeating the examination.

The control unit may be implemented using a processor based electronic circuit which is controlled by an algorithm that also serves to generate the drive signals. The control unit may be implemented as a pure digital circuit, an analog circuit or mixed digital and analog circuits, such as known to the person skilled in the art.

In a second aspect, the invention provides an optical imaging system comprising:
  an optical probe system according to the first aspect,
  a radiation source optically coupled to the optical probe,
    the probe being arranged for guiding radiation emitted from the radiation source to a region of interest, and
  a radiation detector optically coupled to the optical probe,
    the detector being arranged for detecting radiation received from the region of interest.

As mentioned, such optical imaging system is suited within medical applications. E.g. where the optical probe is formed as part of a biopsy needle, where an image of the tissue determined with the optical probe is used to assist taking the biopsy so as to ensure that the biopsy is taken from the desired region.

In a third aspect, the invention provides a method for controlling an optical probe comprising an optical guide having a distal end, a housing, the optical guide being mounted inside the housing so that the distal end is displaceable with respect to the housing, and an electromagnetic actuation system comprising a set of actuators capable of displacing the distal end by a displacement force induced by applying a drive signal to the set of actuators, wherein the method comprises applying a drive signal to the set of actuators so as to displace the distal end according to a scanning form over a field of view, wherein the drive signal provides a scanning frequency which varies according to an amplitude of the drive signal.

It is appreciated that the same advantages and embodiments of the first aspect apply as well for the second and third aspects. In general the various aspects of the invention may be combined and coupled in any way possible within the scope of the invention. These and other aspects, features and/or advantages of the invention will be apparent from and elucidated with reference to the embodiments described hereinafter.

As mentioned, the invention is suitable for medical devices, and especially the invention is suited within the field of cancer diagnosis, monitoring wound healing, or studying molecular processes in tissue. However, it is appreciated that the probe system is suitable also within other fields of application, such as inspecting quality of material surfaces.

BRIEF DESCRIPTION OF THE DRAWINGS

Embodiments of the invention will be described, by way of example only, with reference to the drawings, in which.

DESCRIPTION OF EMBODIMENTS

Figure 1:
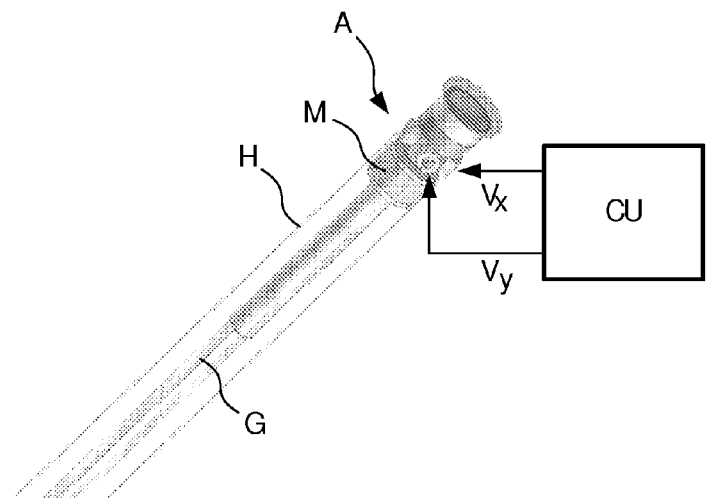
FIG. 1 shows a sketch of an optical probe system with a miniature optical probe suited for medical applications, and a control circuit connected to control actuator coils in the optical probe in order to control movement of an optical guide in the optical probe so as to control the scanning pattern.

FIG. 1 illustrates a drawing of the tip of a miniature optical probe with an optical guide G, an optical fibre, arranged centrally within a housing H (only sketched by a line to ensure visibility of the inner parts of the probe). Hereby light signals can be guided via the optical guide G to the tip of the probe. The optical guide is fixed in relation to the housing in one end, while the distal end of the optical guide, i.e. the end towards the tip of the probe, is free to move. Towards the free distal end, the optical guide G is actuated by an actuation system A. In the shown embodiment, two coil actuators in the form of electromagnetic coils spaced 90° apart are arranged to actuate movement of the optical guide G in two perpendicular directions by application of an appropriate drive signal $V_x$, $V_y$ provided to the two coils from a control unit CU. When a light or ultrasound radiation is applied in the end opposite the free end of the optical guide G, the control unit CU can control movement of the free end of the optical guide G so as to scan over a field of view. According to the invention, the control unit CU generates the drive signals $V_x$, $V_y$ such that a scanning frequency is provided which varies according to an amplitude of the drive signal $V_x$, $V_y$. Hereby, it is possible to scan the field of view such that the scanning frequency varies with the scanning radius. Thus, scanning of smaller radii can be performed with higher scanning frequency than larger radii. Hereby the average scanning speed of a scanning system can be increased compared with systems using a fixed scanning frequency, even without causing problems with overheating the actuator coils.

Figure 2:
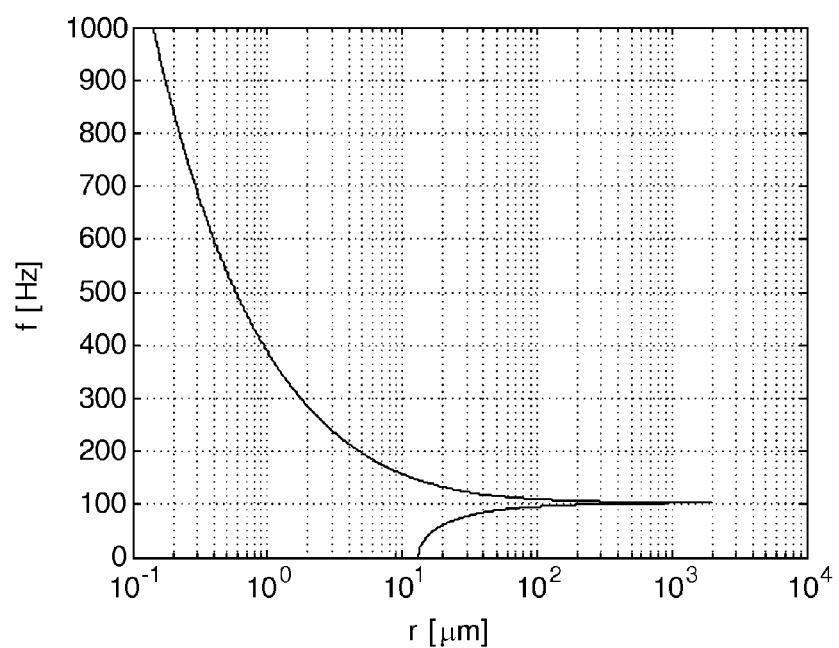
FIG. 2 shows for a graph indicating a relation between scanning radius and scanning frequency for a specific optical probe system embodiment needed in order to achieve a maximal current through the driving coils, where it is seen that the scanning frequency varies significantly according to the scanning radius.

In preferred embodiments the control unit includes a feed-back control loop that provides a scanning frequency with a drive current through the coils being kept substantially equal to the maximally allowed currents through the coils. Hereby the maximum scanning speed over the field of view can be obtained. A spiral scanning form can advantageously be used. A measuring coil M attached to the optical guide G is included to allow feed-back of the actual position of the optical guide G during the scanning FIG. 2 shows a graph illustrating for a specific optical probe configuration, an example of a relation between scanning radius r and scanning frequency f in order to provide a maximal allowed current to the driving coils. As seen, the drive signals to the actuators are generated such that the scanning frequency f varies significantly with the actual scanning radius r, namely such that smaller radii are scanned at higher frequencies than larger radii for the same maximal allowed current. Thus, when circles are scanned with the maximum allowed drive current but at varying frequency, the radius that can be reached will be a function of frequency. Or stated in reverse: for a given radius, there is a maximum frequency at which a circle with that radius can be scanned, using the maximum allowed driving current. The curve shown in FIG. 2 is based on analysis of a specific optical probe system, and the curve illustrates the estimated relating maximum radius and maximum frequency. The area surrounded by the curve and the lines f=0 and radius=0, represents the set of all possible frequencies and radii which can be used without overheating the given actuator. In practice, it should be taken into account that there is an additional geometric constraint on the radius: the radius should always smaller than r_max (in the specific system r_max=100 μm). Also, there is a separate upper limit on the scanning frequency, since the scanning frequency is not only limited by the dissipation in the driving coils but also by parameters of the feed-back control loop (in the specific system this feed-back limitation is 300 Hz).

In a specific optical probe embodiment, a circular field of view with a maximum diameter of 200 μm can be imaged. Furthermore, the maximum amplitude of AC current through the driving coils at room temperature is 0.42 A. The (lowest) resonance frequency of the system is at 103 Hz. If a circle with diameter of 200 μm is scanned at the resonance frequency of 103 Hz, an AC current of 0.0204 A amplitude is needed. The same line can be scanned with the maximum current (amplitude of 0.42 A) at the higher frequency of 109.5 Hz. When a circle with a diameter of only 20 μm is scanned at the resonance frequency, a current amplitude of only 0.002 A is needed, while the same circle can be scanned using the maximum current amplitude of 0.42 A at the much higher frequency of 156.7 Hz.

In order to give an estimate about how much it is possible to increase the scanning speed in this way two examples will be given, based on the above mentioned optical probe, i.e. in a system with a maximal scanning frequency of 300 Hz. When scanning a circular field, scanning can be performed in spirals with distance of 0.5 μm between them. Scanning an area of 150 μm in diameter at the resonant frequency only, then an image is obtained in a time of 1.46 seconds. However, by adopt the a varying scanning frequency such that the maximal possible current of 0.42 A is always running through the coils during scanning of the whole field of view, the same image (150 μm diameter) can be obtained in a time of only 1.17 seconds. Next, if a smaller area with a diameter of only 50 μm is scanned, then when scanning at only resonant frequency an image can be captured in 0.49 seconds (2 frames per second). However, when scanning is performed while adapting the varying scanning frequency, then an image can be obtained in 0.32 seconds (3 frames per second).

It should be stressed that the maximum current which can run through the driving coils is determined by the temperature of the coil. Therefore, in order to drive the scanner at the maximum current, it is preferred to measure temperature of the driving coils rather than measuring the driving current. Temperature of the coils is related to its electrical resistance as $R=R_0(1-\alpha(T-T_0))$ where R is coil resistance at temperature T, $R_0$ represents coil resistance at temperature $T_0$, and $\alpha$ represents temperature coefficient of resistance of the coil. The electrical resistance of the coil can be obtained by measuring voltage and current running through the coil. Alternatively, a temperature sensor can be used to measure coil temperature, however within medical miniature equipment it is advantageously to save space to such temperature sensor and instead use the mentioned electrical temperature deduction method.

Figure 3:
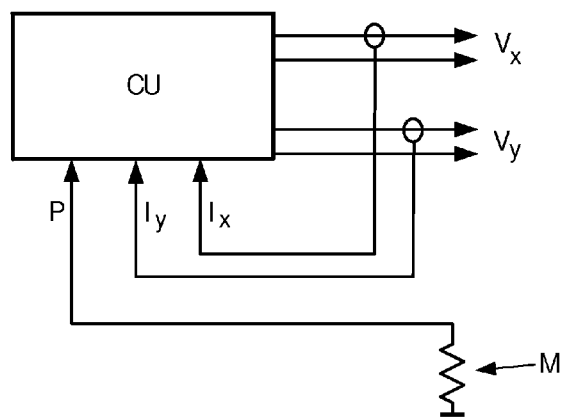
FIG. 3 shows a diagram of a control unit embodiment generating a set of two electric drive signals to respective two actuators, and as a feedback, the control unit is connected to a measuring coil serving to monitor the position of the optical guide.

FIG. 3 illustrates a simple diagram of a control unit CU. The control unit CU generates a set of two drive voltages $V_x$, $V_y$ to a set of respective actuators, e.g. two drive coils. The resulting drive currents $I_x$, $I_y$ are determined and fed back to the control unit which can then adjust the drive voltages $V_x$, $V_y$ accordingly, e.g. in case a predefined current limit is obtained for one of the actuators. Further, a measuring transducer in the form of a measuring coil attached in relation to the optical guide to monitor its position and thus feed-back a position signal P to the control unit CU. Hereby the control unit CU can take into account the actual position of the optical guide in the generation of the drive voltages $V_x$, $V_y$.

Figure 4:
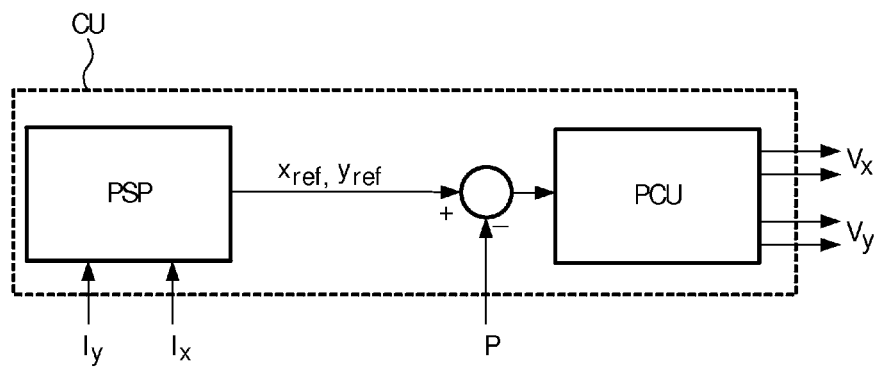
FIG. 4 shows in more details an example of implementation of the control unit of FIG. 3 with a position set-point generator and a position control unit.

FIG. 4 illustrates a possible implementation of the control unit of FIG. 3. A position set-point generator PSP generates a set of reference positions or preferred x and y positions $x_{ref}$, $y_{ref}$. In a preferred embodiment, this set has the form:

$$x_{ref}=k\omega t \sin(\omega t), \text{ and}$$

$$y_{ref}=k\omega t \sin(\omega t+\pi/2),$$

where the scanning frequency is denoted ω, time is denoted t, and k is a parameter given. This preferred position is then subtracted by the actual x and y positions P based on the measurement coil input. The result of this subtraction is applied to a position control unit PCU which then generates the drive signals $V_x$, $V_y$ accordingly. The position set-point generator PSP can determine the scanning frequency ω based on the feed-back in the form of the drive currents $I_x$, $I_y$ through the actuators, e.g. by providing the highest possible scanning frequency ω taking into account a simple maximum current limitation, such as mentioned.

Figure 5:
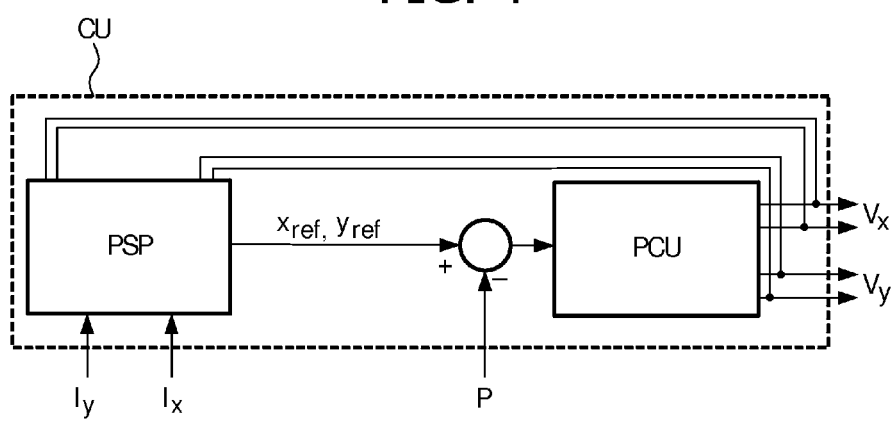
FIG. 5 shows an alternative implementation of the control unit of FIG. 3, namely where the set-point generator receives as feedback a measure of temperature of the drive coils by measuring related current and voltage applied to the drive coils.

FIG. 5 illustrates an alternative embodiment of the control unit similar to the one of FIG. 4, expect that the position set-point generator PSP receives the drive signals $V_x$, $V_y$, thereby allowing the position set-point generator PSP to generate the preferred set of positions $x_{ref}$, $y_{ref}$ taking into account the actual temperature of the drive coils derived by determining from the drive voltages $V_x$, $V_y$ and drive currents $I_x$, $I_y$. Hereby it is e.g. possible to constantly optimize scanning frequency ω up to a predetermined maximum coil temperature which is considered to provide safe operation. Thus, the potential of the system is used provide maximum scanning speed.

Figure 6:
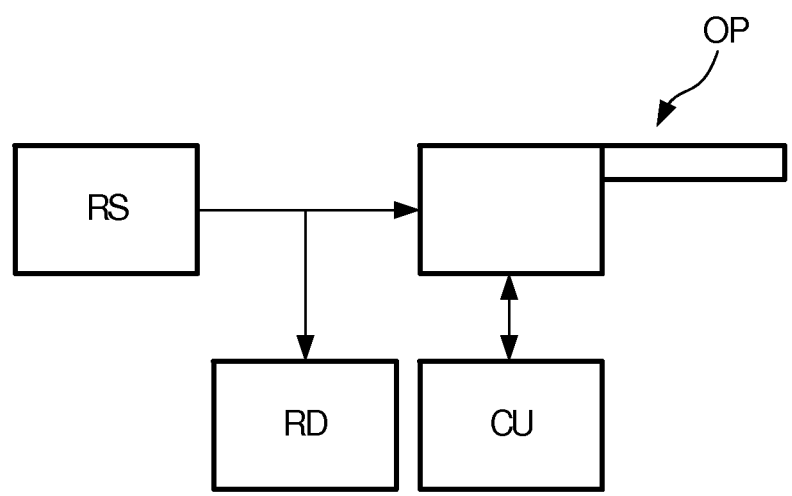
FIG. 6 shows a diagram of an optical imaging system embodiment.

FIG. 6 illustrates a diagram of an optical imaging system comprising an optical probe system as described in the foregoing. A radiation source RS, e.g. a laser or LED based signal source, is optically coupled to the optical probe OP, e.g. a miniature optical probe for medical examination and/or biopsy sampling. The probe OP is arranged for guiding radiation emitted from the radiation source RS to a region of interest. A radiation detector RD is optically coupled to the optical probe OP, and this detector RD is arranged for detecting radiation received from the region of interest. From the received radiation detected by the detector RD, it is possible to create an image of the region of interest. In case of a biopsy sampling system, the probe OP can form part of the biopsy needle, and thus it is possible to obtain an image from the actual biopsy sampling site. This is highly advantageous to ensure that the biopsy is taken from the desired location in the tissue. With the optical probe system according to the invention, scanning and thereby imaging can be performed at a high speed, thus reducing the time required for the medical treatment.

To sum up, the invention provides an optical probe system having a probe with an optical guide G with a distal end. The optical guide G is mounted inside a housing H so that the distal end is displaceable with respect to the housing H. A set of actuators A, e.g. electromagnetic drive coils, can displace the distal end by application of a drive signal Vx, Vy. A control unit CU generates the drive signal Vx, Vy so as to provide a scanning frequency which varies according to an amplitude of the drive signal Vx, Vy. With such probe system it is possible to scan a field of view with a scanning frequency that varies with the scanning radius. Taking into account the maximum allowable drive current, it is possible to increase scanning speed compared to scanning at the mechanical resonance frequency of the optical system, since small radii can be scanned at a high scanning frequency. The probe system is suitable for miniature medical devices, e.g. as part of a biopsy needle, where the probe can be used to provide on-site images assisting a medical staff in taking the biopsy in the desired location, e.g. to ensure that a biopsy sample is taken from a tumor and not the surrounding tissue. In an embodiment, the actuators are electromagnetic coils, and wherein the control unit CU generates the drive signal Vx, Vy taking into account the temperature of the actuator coils, such that maximum scanning speed can be obtained still without overheating the drive coils. Especially, the coil temperature can be deducted based on a measurement of the electrical resistance of the coil, i.e. based on the drive signal current and voltage. Further, a measuring coil M may be attached to the optical guide G to allow positional feed-back so as to allow the control unit CU to generate a drive signal Vx, Vy for precisely obtaining a desired scanning pattern.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An optical probe system comprising:
a probe comprising
an optical guide (G) having a distal end,
a housing (H), the optical guide (G) being mounted inside the housing (H) so that the distal end is displaceable with respect to the housing (H), and
an actuation system (A) comprising a set of actuators capable of displacing the distal end by a displacement force induced by applying a drive signal ($V_x$, $V_y$) to the set of actuators, and
a control unit (CU) operationally connected to the probe, the control unit (CU) being arranged to generate the drive signal ($V_x$, $V_y$) to the set of actuators so as to displace the distal end according to a scanning form over a field of view, wherein the control unit (CU) generates the drive signal ($V_x$, $V_y$) so as to provide a scanning frequency which varies according to an amplitude of the drive signal ($V_x$, $V_y$).

2. Optical probe system according to claim 1, wherein the control unit (CU) is arranged to generate the drive signal ($V_x$, $V_y$) such that the amplitude of the drive signal ($V_x$, $V_y$) varies during scanning over a field of view.

3. Optical probe system according to claim 1, wherein the drive signal ($V_x$, $V_y$) to the set of actuators comprises a set of harmonic signals.

4. Optical probe system according to claim 1, wherein the set of actuators comprises at least one of: an electrically conductive coil, and a piezoelectric element.

5. Optical probe system according to claim 1, wherein the scanning form over a field of view is one of: a spiral form, and Lissajous figures.

6. Optical probe system according to claim 1, wherein the drive signal ($V_x$, $V_y$) is limited in accordance with a predefined maximum value determined by the set of actuators.

7. Optical probe system according to claim 1, wherein the drive signal ($V_x$, $V_y$) is limited in accordance with a measure of temperature of the set of actuators.

8. Optical probe system according to claim 7, wherein the set of actuators are electrically conductive coils, and wherein the measure of temperature of the electrically conductive coils is deducted by measurement of electrical resistance of at least one of the electrically conductive coils.

9. Optical probe system according to claim 1, comprising a measuring transducer (M) arranged to measure a position (P) of the optical guide (G).

10. Optical probe system according to claim 9, wherein the control unit (CU) comprises a position set-point generator (PSP) and a position-control unit (PCU), wherein the position-control unit (PCU) is operationally connected to the measuring transducer (M).

11. Optical probe system according to claim 1, wherein the optical guide (G) is an optical fibre with a free distal end.

12. Optical probe system according to claim 1, arranged for confocal scanning.

13. Optical proble system according to claim 1, wherein the optical probe forms part of one of: an endoscope, a catheter, a needle or a biopsy sample system.

14. An optical imaging system comprising:
   an optical probe system according to claim 1,
   a radiation source (RS) optically coupled to the optical probe (OP), the probe (OP) being arranged for guiding radiation emitted from the radiation source (RS) to a region of interest, and
   a radiation detector (RD) optically coupled to the optical probe (OP), the detector (RD) being arranged for detecting radiation received from the region of interest.

15. Method for controlling an optical probe comprising an optical guide having a distal end, a housing, the optical guide being mounted inside the housing so that the distal end is displaceable with respect to the housing, and an electromagnetic actuation system comprising a set of actuators capable of displacing the distal end by a displacement force induced by applying a drive signal to the set of actuators, wherein the method comprises applying a drive signal to the set of actuators so as to displace the distal end according to a scanning form over a field of view, wherein the drive signal provides a scanning frequency which varies according to an amplitude of the drive signal.

* * * * *